United States Patent [19]
Becquet

[11] Patent Number: 5,824,836
[45] Date of Patent: *Oct. 20, 1998

[54] PROCESSING SYSTEM FOR CONDENSING HYDROCARBON EMISSIONS FROM A VAPOR STREAM

[76] Inventor: James W. Becquet, 113 Pigeon Loop, Lafayette, La. 70508

[ * ] Notice: This patent issued on a continued prosecution application filed under 37 CFR 1.53(d), and is subject to the twenty year patent term provisions of 35 U.S.C. 154(a)(2).

[21] Appl. No.: 665,668
[22] Filed: Jun. 20, 1996
[51] Int. Cl.$^6$ ........................................... C07C 7/00
[52] U.S. Cl. ..................... 585/800; 208/340; 203/18; 165/113; 202/185.3; 202/185.5; 202/185.6
[58] Field of Search ............................ 585/800; 208/340; 203/18; 165/113; 202/185.3, 185.5, 185.6

[56] References Cited

U.S. PATENT DOCUMENTS 5,346,537  9/1994  Lowell ........................................ 95/161

Primary Examiner—Glenn Caldarola
Assistant Examiner—In Suk Bullock
Attorney, Agent, or Firm—Domingue, Delaune & Waddell

[57] ABSTRACT

A system for lowering the ambient temperature of a vapor being produced from a glycol dehydrator unit, as well as a system for reducing the emissions of BTEX is disclosed. Generally, the system comprises a condenser for condensing the vapor into a fluid phase and a gas phase, and a storage tank, fluidly connected to the outlet of the condenser. The system will also contain a pump member, operatively associated with the storage tank, adapted for pumping the fluid phase from the storage tank; and, a activating member adapted for activating the pump means after the fluid phase reaches a predetermined level within the storage tank. The system will include as part of the condenser member a turbine associated with a roof, with the roof being generally positioned over the condenser coils so as to shade the condenser coils. A method of recovering hydrocarbons from a vapor phase as well as lowering the ambient temperature is also disclosed.

7 Claims, 3 Drawing Sheets

PROCESSING SYSTEM FOR CONDENSING HYDROCARBON EMISSIONS FROM A VAPOR STREAM

BACKGROUND OF THE INVENTION

This invention relates to a process and system for handling a vapor stream. More particularly, but not by way of limitation, this invention relates to a process and method for recovery of hydrocarbons from a vapor stream as well as reducing the ambient temperature of the gas phase and condensed liquid phase. The invention herein disclosed also relates to an air pollution control device.

In the production of hydrocarbons, a well is completed to a hydrocarbon bearing reservoir. The production from the reservoir will entail the production of oil, gas and in-situ water. Once the production of fluids and gas has reached the surface facilities, the operators will be required to separate the oil phase, gas phase, and water phase so the hydrocarbons may be transported to gathering sites.

The gas phase of the production stream will contain various types of hydrocarbons such as methane and ethane. The liquid phase will contain larger molecules such as propane, butane and pentane. Other more complex molecules such as benzene, toluene, and xylene may also be found within the production stream. Also entrained within the gas phase will be dispersed water molecules. Operators find it highly desirable to further separate the water molecules from the hydrocarbons since the water molecules may form hydrates in flow lines and pipelines.

A significant method of dehydrating the gas phase is the use of glycol dehydrators. As is understood by those of ordinary skill in the art, the glycol dehydrators will separate the water phase by use of glycol and the application of heat. The resultant natural gas stream is generally devoid of water molecules. The water removed from the natural gas is emitted from the glycol dehydrator in a vapor phase, with said vapor phase containing hydrocarbon fluids, hydrocarbon gas and water. Typically, this vapor phase is emitted into the atmosphere. Due to the application of heat, the ambient temperature of the vapor stream exiting the glycol dehydrator is approximately 212 degrees Fahrenheit.

As noted earlier, some of the hydrocarbon substituents include benzene, toluene, ethylbenzene, and xylene (hereinafter referred to as "BTEX"). The BTEX molecules have been found to be a carcinogen, and thus, the BTEX compounds are considered hazardous. Both State and Federal governments have regulatory statutes that limit the introduction of BTEX into the atmosphere. Further, State and Federal governments have rules that require operators of applicable existing glycol dehydrator units utilize a cooling system that provides for the final exhaust temperature of the gas and liquid phase of less than 110 degrees F.

Thus, there is a need for a system that will allow the economical reduction of BTEX emissions. There is also a need for a process that will allow for the reduction of the final exhaust temperature from glycol dehydrator units.

SUMMARY OF THE INVENTION

A system for lowering the ambient temperature of a vapor being produced from a glycol dehydrator unit, as well as a system for reducing the emissions of BTEX is disclosed. Generally, the system comprises a condenser means for condensing the vapor into a fluid phase and a gas phase, and a storage tank, fluidly connected to the outlet of the condenser means. The system will also contain a pump member, operatively associated with the storage tank, adapted for pumping the fluid phase from the storage tank; and, activating means for activating the pump means after the fluid phase reaches a predetermined level within the storage tank.

The system may further comprise a vent means, operatively associated with the storage tank, for venting the gas phase from the storage tank. In the preferred embodiment, the condenser means includes a wind turbine associated with a roof, with the roof being generally positioned over the condenser coils so as to shade the condenser coils.

The system will also contain a temperature gauge that can be positioned at various sampling points so as monitor the temperature of the vapor as the stream makes its way through the system. In the preferred embodiment, the system will contain a secondary containment dike, operatively associated with the storage tank, for containing the storage tank in case of a spill or leak.

A method of recovering hydrocarbons from a vapor phase as well as lowering the ambient temperature is also disclosed. Generally, the method comprises flowing the vapor phase from a glycol dehydrator unit, and directing the vapor phase to the recovery system. Next, the vapor phase is allowed to condense within the heat exchanger and wherein the vapor condenses to a fluid phase and a gas phase. Thereafter, the fluid and gas phase is delivered to a storage tank member. It should be noted that the heat exchanger (and the stream therein) is being cooled via the roof and fan means associated with the system. Further, the ambient temperature of the fluid and gas phase is allowed to continue to decrease in the storage tank via thermal mass cooling caused by the diurnal temperature drop. Remember, since the process herein described is continuous, the mass may be cooled especially during the night as the mass seeks the average ambient temperature.

The method may further include venting the remaining gas phase within the storage tank into the atmosphere, and pumping the fluid phase from the storage tank to a reservoir means for storing the fluid phase via a pump member. It should be noted that the step of venting the gas phase into the atmosphere may include preventing any adverse backpressure (such as the pressure of the gas phase within the storage tank) that may be delivered to the glycol dehydrator unit.

In one embodiment, the step of pumping the fluid phase from the storage tank to the reservoir means includes measuring the fluid phase level within said storage tank and thereafter activating the pump member once a predetermined level is reached within the storage tank. Next, the operator may terminate the pump once the fluid phase level has been lowered due to the pumping. Of course, the system herein described may be fully automated so that human operation is not necessary.

In another embodiment, the recovery system contains a temperature gauge adapted to the storage tank, and the method would further comprise monitoring the output temperature of the fluid phase being pumped from the storage tank, and thereafter, adjusting the liquid level to provide for longer retention time in accordance with the temperature of the fluid phase.

An advantage of the present system includes lowering the emissions of hazardous compounds such as volatile organic compounds and aromatic molecules including benzene, toluene, and xylene, that are emitted from process facilities. Another advantage is that the system herein described lowers the average final exhaust of a vapor stream to comply with Federal and State regulatory law. Still yet another advantage includes the system is maintained without the use of electricity, power input and/or water input for significant energy savings.

Another advantage includes the distillate recovered pursuant to the process may then be placed in the sales line and thereafter sold. Yet another advantage includes having a secondary containment tank. Still another advantage is the system is explosion proof. Yet another advantage includes that no back pressure is put on the glycol dehydrator vent which if back pressure is placed on the glycol dehydrator, the boiler may rupture. The list of advantages herein set out is meant to be illustrative.

DESCRIPTION OF THE PREFERRED EMBODIMENTS

Figure 1:
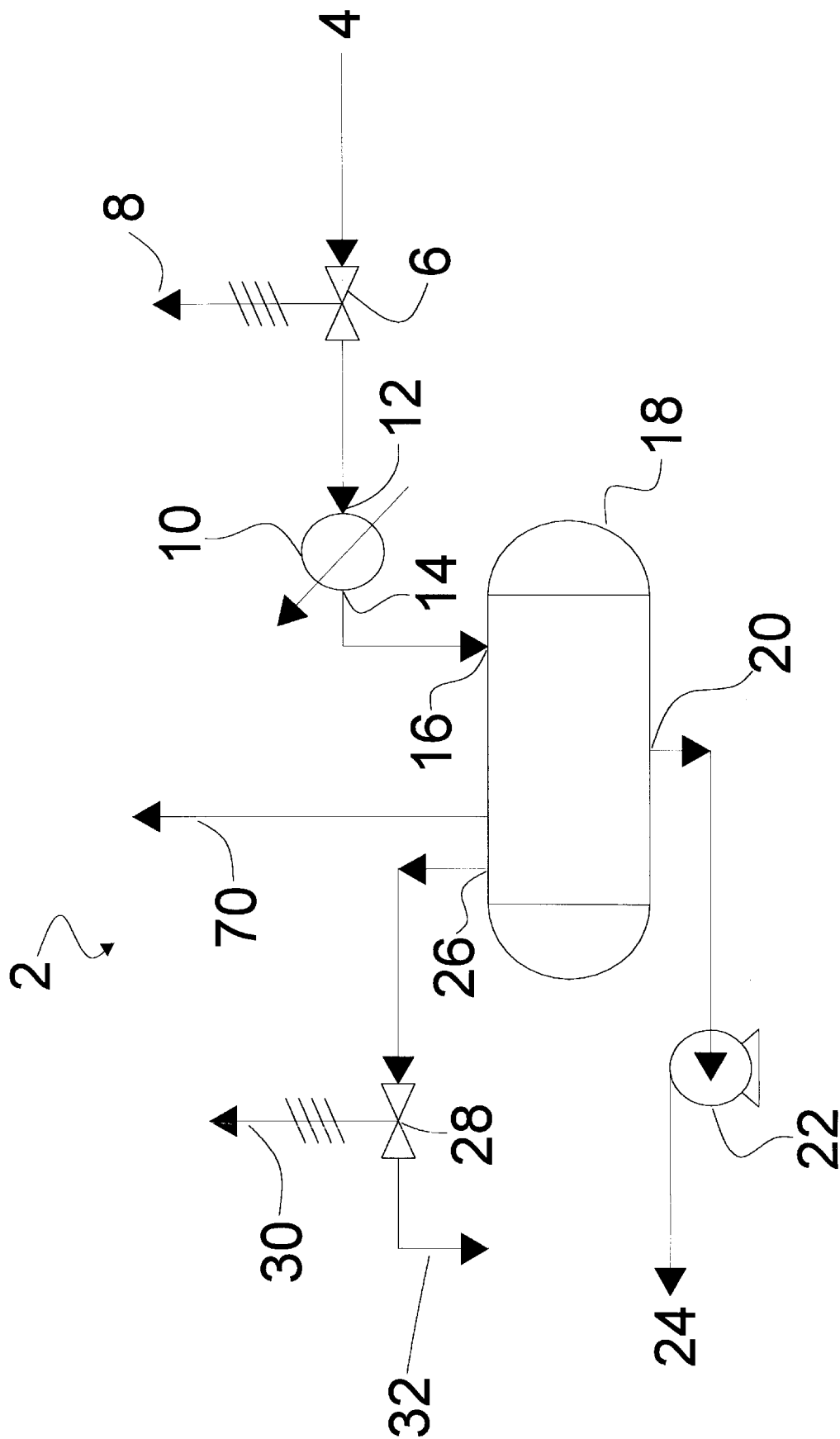
FIG. 1 is a process flow diagram of the present invention.

Referring to FIG. 1, a process flow diagram 2 of the present invention is shown. In accordance with the teachings of this invention, the vapor stream which will be exiting the glycol dehydrator unit 4 will be directed to a relief valve 6 that has operatively associated therewith a vent means 8 for venting the vapor stream. It should be noted that the invention is applicable to any type of glycol dehydrator unit. The relieve valve 6 is inserted into the system in order to release the vapor in case of an upset in the downstream components such that flow through the system is restricted or terminated.

The vapor stream will be directed to the novel condenser means 10 for condensing the vapor stream into a fluid phase and gas phase with the vapor stream being directed into the condenser means via the inlet portion 12. The condenser means 10 includes a heat exchange coil member, roof member, and a wind driven turbine fan member as will be more fully set out later in the application. As the vapor stream is directed through the condenser means 10, the novel features of condensing the vapor stream in tandem with cooling of the vapor stream is accomplished.

The condensed and cooled fluid phase and gas phase will exit the condenser means 10 at the outlet portion 14 and in turn the stream will be directed to the inlet portion 16 of the storage tank 18. The liquid phase and gas phase within the storage tank 18 allows for the thermal mass cooling of the liquid and gas phase, as well as allowing the accumulation of the liquids and gas. Thus, as the liquids and gas collect within the storage tank 18, the contents are allowed to cool due to the cooling of the material mass with the surface temperature which is particularly effective during the night time hours. Also, there may be placed within the tank 18 an expandable metal screen (not shown) that is in contact with the gas as the gas passes from the tank 18 to the vent 70.

The storage tank 18 is provided with a pump outlet 20 which ultimately delivers the liquid phase to a transfer pump 22 for pumping the stream to other production facilities. For instance, the stream may be delivered to a low pressure production separator 24 for further separation of the oil, gas and water phase which may be present. Alternatively, the stream may be delivered to a heater treater 24. Nevertheless, the distillate thus collected from the vapors via the novel process may be ultimately sold by the operator.

The storage tank 18 will also contain a relief outlet 26 for directing the stream to a relief valve 28. Generally, the relief valve 28 is provided in case the flow through the storage tank 18 becomes, for instance, restricted or terminated and the operator finds it necessary to redirect flow and/or relieve pressure. As noted earlier, the entire system may be automated, and thus, the system may automatically perform these functions. The relief valve 28 will have operatively associated therewith a vent member 30 for venting the gas phase into the atmosphere and/or to other production facilities. Also associated therewith is the liquid line means 32 for directing the liquid phase thus discharged to the proper production handling facilities (not shown).

Figure 2:
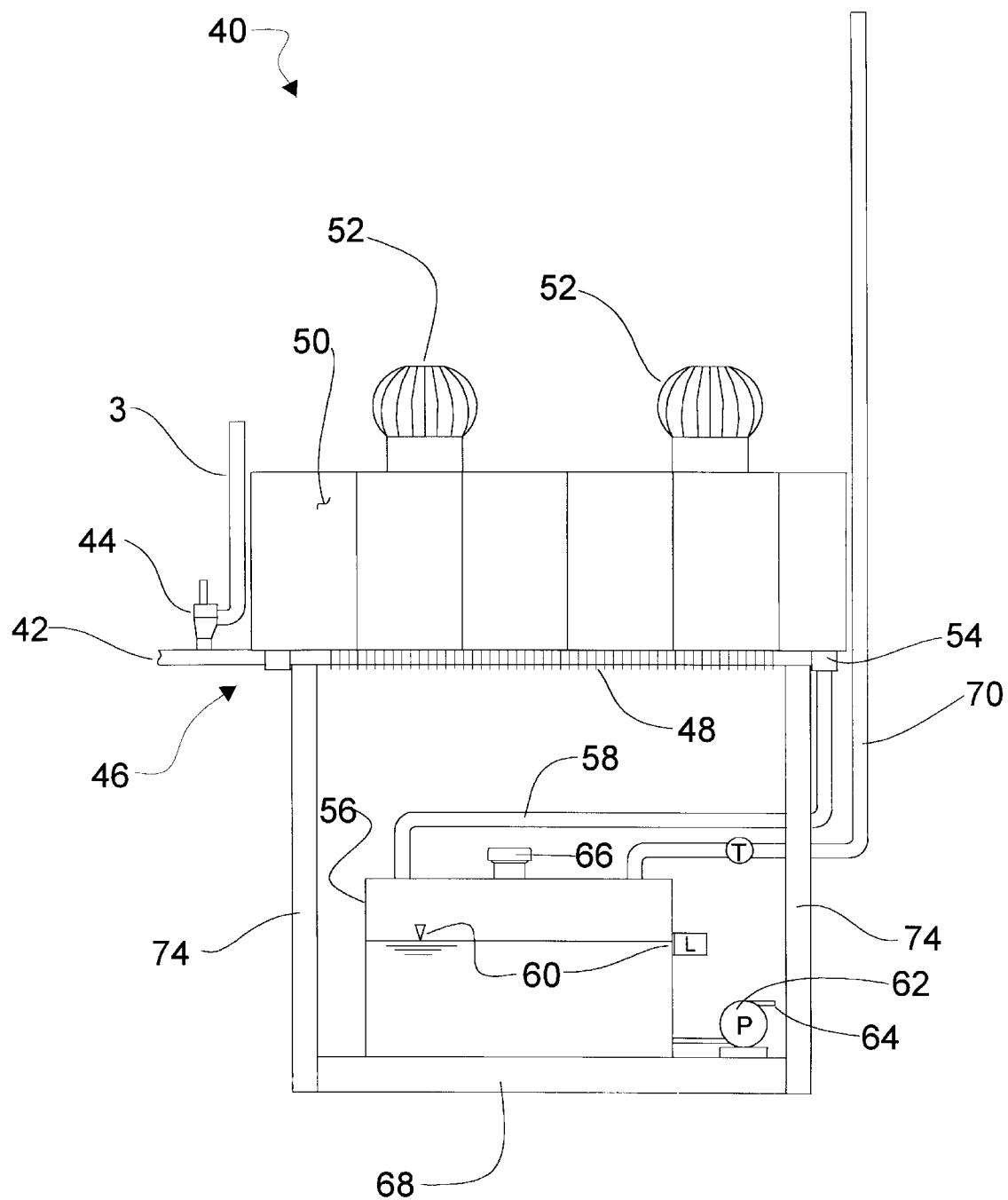
FIG. 2 is a schematic illustration of the preferred embodiment of this invention.

Referring now to FIG. 2, the preferred embodiment of this invention will now be described. The system 40 includes an inlet 42 from the specific process facility, which in the preferred embodiment will be a glycol dehydrator unit (not shown). The inlet 42 will have operatively associated therewith a safety relief valve 44, such as the type purchased from Taylor Tools Inc. under the mark Series 8400 Johnson Vapor Valve. The safety relief valve 44 may be designed so that opening will be effected when either the gas pressure and/or liquid pressure exceeds a predetermined level. The safety relief valve 44 will have operatively associated therewith a relief vent for venting the released liquids and/or gas as is well understood by those of ordinary skill in the art.

In the normal operation of the system 40, the vapor stream emanating from the glycol dehydrator unit will thus be directed to the novel condenser means 46 for condensing and cooling the vapor stream. In the preferred embodiment, the novel condenser means includes the heat exchanger 48, the insulated roof 50, and the pair of high efficiency wind turbines 52. The heat exchanger 48 is of the type that is type that is commercially available from Air Pollution Controls Inc. The wind turbines 52 are commercially available from Empire Inc. under the mark TU 126. The roof may contain insulation to aid in protection from the sun.

Thus, the vapor stream will be directed through the condenser means 46 via the heat exchange 48. The actual coils of the heat exchange 48 are shielded from the sun by the roof 50. Further, the wind turbine fans 52 will act to create a circulation within the apex of the roof by drawing the air above the heat exchanger 48 and in turn drawing fresh air from the outside area into the underside of the roof.

Thus, the vapor stream will be condensed and cooled following the path herein discussed. From the heat exchanger 48 outlet 54, the fluid phase and gas phase will be directed to the storage tank 56 via the flow line 58. The storage tank 56 will serve to store the liquids and gas which has been transported through the condenser means 46. The retention time of the material mass within the storage tank will allow for thermal mass cooling (also referred to as diurnal cooling). It should also be noted that the expanded metal screen within the tank 56 contacts the hot gas and cooled liquid causing added cooling to the gas phase.

The storage tank 56 will have adapted thereto for operation a liquid level means 60 for determining the liquid level of the storage tank, and once a predetermined height has been reached, the liquid level will produce an indicative signal which will ultimately activate the control pump means 62 for pumping the liquid contents from the storage tank 56. An example of a liquid level means 60 is commercially available from Frank W. Murphy Co. under the mark L 1200N DVD.

As noted in the process flow diagram 2, the output 64 from the control pump means 62 will be directed to a production separator for further separation of the oil, gas and water phase which may be present. Alternatively, the stream may be delivered to a heater treater 24. Nevertheless, the hydrocarbon emissions thus collected via the novel process may be ultimately sold by the operator.

The storage tank 56 will also have adapted thereto a float relief valve 66. The relief valve 66 is a safety type of valve ensuring that if the liquid level within the storage tank 56 raises to the top of the storage tank 56, the valve will open thereby allowing the liquid to empty from the tank. In the preferred embodiment, the storage tank 56 will be positioned within a secondary containment vessel 68 so that any liquid may be received therein. The float relief valve 66 may also be pressure sensitive so that after a predetermined pressure level has been reached within said storage tank 56, the relief valve 66 will open. The float relief valve 66 is commercially available from Clay & Baily Co. under the mark 369M.

The vent line 70 has also been provided in the preferred embodiment. The vent line 70 serves as an outlet for the gas phase that has accumulated within the storage tank 56 pursuant to the process described. As shown in FIG. 2, the vent line 70 allows the gas phase to exit into the atmosphere. Thus, this system of open vent puts no back pressure on the glycol dehydrator boiler. It is possible, however, to have the vent line connected to a gas separator for further processing and eventual sale. Alternatively, the gas phase may be used, for instance, as fuel gas for the processing facility.

The vent line 70 will have associated therewith a temperature gauge 72 which will monitor the temperature of the gas phase that is within the vent line 70. The operator may deem it advisable to have other temperature gauges at other various points within the system in order to monitor the temperature at various points. Thus, it is possible to have a temperature gauge operatively associated with the storage tank 56 so that the ambient temperature of the material mass within the storage tank 56 is monitored. In the event that the temperature of the material mass is higher than desired, the operator may adjust various parameters within said system. For instance, the operator may check the wind turbines to make sure they are operating properly. Alternatively, the operator may adjust the liquid level means 60 so that there is more time for the thermal mass cooling within the tank 56 i.e. allowing the liquid level to rise higher before the control pump means 62 is activated thereby pumping the liquid phase from the storage tank 56.

In the preferred embodiment, the system 40 is contained in a modular form, sometimes referred to as a skid. Thus, the roof 50 is supported by the lateral members 74, with the lateral members being connected at one end to the roof 50 and at the second end to the secondary containment vessel 68. The lateral members 74 may be connected to the roof and containment vessel 68 by any conventional means such as welding. Thus, except for the inlet 42 connection from the glycol dehydrator unit, the system 40 may be fabricated at a construction site, and the entire unit may be transported to the well site.

Figure 3:
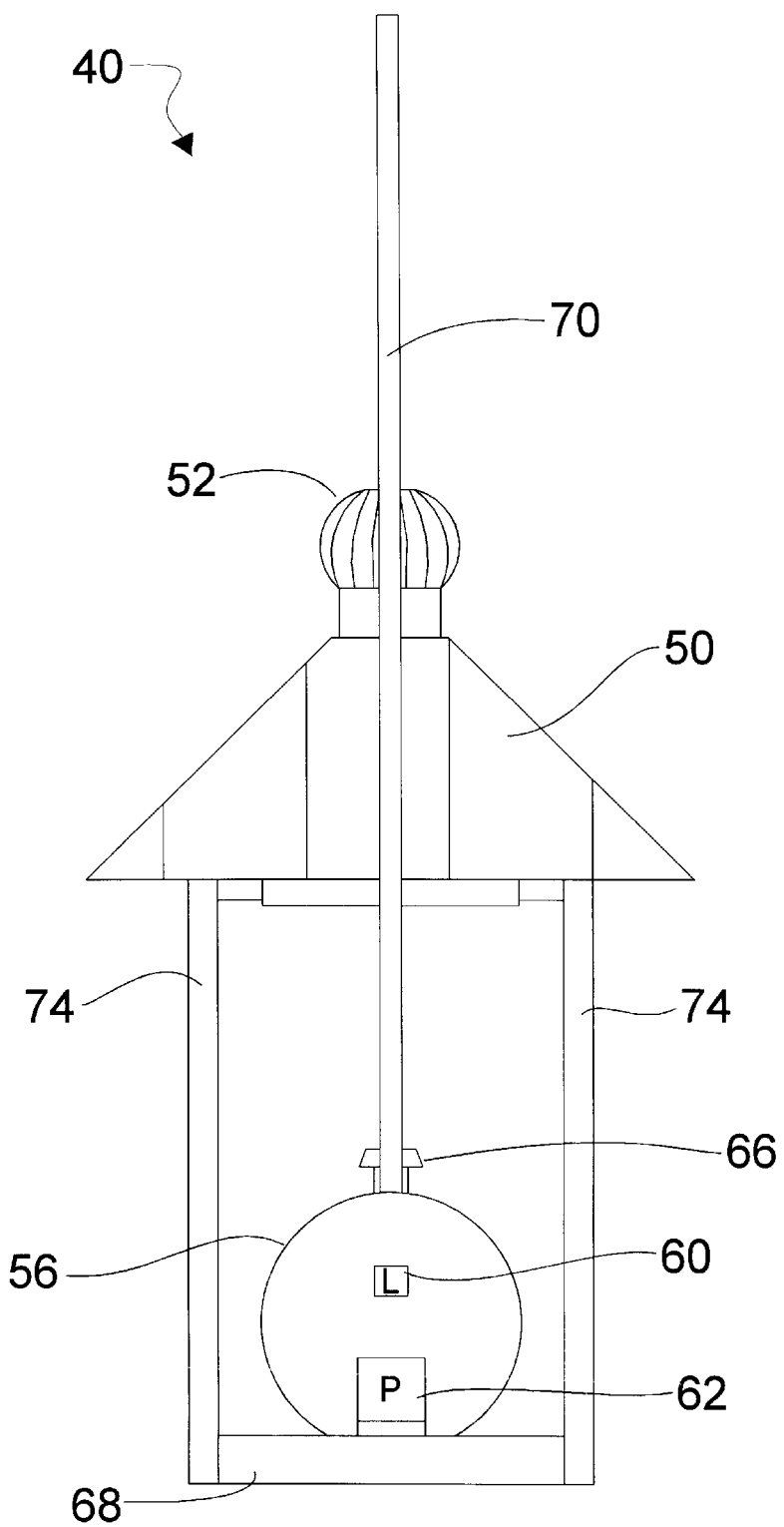
FIG. 3 is a side view of the embodiment depicted in FIG. 2.

Referring to FIG. 3, a side view of the preferred embodiment of FIG. 2 is illustrated. The roof 50 has been mounted on the lateral support members 74. FIG. 3 shows the positioning of the wind turbine 52. Thus, the roof 50 and turbines 52 act to cool the heat exchanger 48 and the storage tank 56 via the shade of the roof 50 as well as air circulation of the turbines 52.

In operation, the method may include flowing the vapor phase from a glycol dehydrator unit 4, and directing the vapor phase to the recovery system 40. Next, the vapor phase is allowed to condense within the heat exchanger 48 to a fluid phase and a gas phase. Thereafter, the fluid and gas phase is delivered to the storage tank 56. It should be noted that the heat exchanger 48 is being cooled via the roof 50 and fan means 52 associated with the system 40. Further, the ambient temperature of the fluid phase is allowed to continue to decrease in the storage tank via the diurnal effect with the passage of time as well as the expanded metal screen. This is known as thermal mass cooling. On warmer days, it may be necessary to have longer retention times.

The method may further include venting the remaining gas phase within the storage tank 56 into the atmosphere, and pumping the fluid phase from the storage tank 56 to other process facilities (such as a low pressure separator) with a pump member 62. In one embodiment, the step of pumping the fluid phase from the storage tank 56 to the process facilities includes measuring the fluid phase level within said storage tank 56 and thereafter activating the pump member 62 once a predetermined level is reached within the storage tank 56. Next, the operator may terminate the pump 62 once the fluid phase level has been lowered due to the pumping (remember, this function may also be automated).

In preferred embodiment, the recovery system contains a temperature gauge adapted to the vent line 70, and the method would further comprises monitoring the output temperature of the gas phase exiting from the storage tank 56. If the exiting temperature is too high, the operator may make adjustment to the condenser means. Also, the operator may have a temperature gauge associated with the storage tank 56, and if the exiting temperature is too high, the operator may adjust the liquid level to provide for longer retention time in accordance with the temperature of the fluid phase.

Changes and modifications in the specifically described embodiments can be carried out without departing from the scope of the invention which is intended to be limited only by the scope of the appended claims.

I claim:

1. A process for condensing hydrocarbon emissions from a vapor stream and lowering an ambient temperature of the hydrocarbon emissions, the process comprising:

flowing the vapor stream from a dehydrator unit;

directing the vapor stream to a condenser means for condensing the vapor stream into a liquid phase and gas phase, and wherein said condenser means comprises: a series of heat exchange coils adapted so that the vapor stream is directed through said heat exchange coils; a roof member positioned above said heat exchange coils so that a shaded area is provided; and a fan, operatively associated with said roof member, for circulating the air through said roof member;

delivering the liquid phase into a storage tank, said storage tank being positioned within said shaded area;

providing said shaded area above said heat exchange coils so that the ambient temperature of said liquid phase decreases;

rotating said fan by importing a wind through said fan, venting the air from said roof member into the atmosphere so that the ambient temperature of said liquid phase decreases;

allowing the ambient temperature of said liquid phase in said storage tank to decrease by thermal mass cooling;

discharging the gas phase into the atmosphere;

pumping the liquid phase from the storage tank to a reservoir means for storing the fluid phase with a pump member.

2. The process of claim 1 wherein the step of pumping the liquid phase from the storage tank to the reservoir means includes:

measuring the liquid phase level within said storage tank;

activating said pump member once a predetermined level is reached within said storage tank;

terminating said pump member once the liquid phase level has been lowered due to said pumping.

3. A method of recovering hydrocarbons from a vapor phase, and wherein the method comprises:

flowing the vapor phase from a glycol dehydrator unit;

directing the vapor phase to a recovery system, said recovery system containing:

a heat exchange member; a roof positioned above said heat exchange member; and, a fan member adapted to said roof so as to circulate an air from said roof;

allowing the vapor phase to condense to a liquid phase and a gas phase within said heat exchange member;

delivering the liquid phase and gas phase to a storage tank member, said storage tank member being in a shaded area from said roof;

providing said shaded area over said heat exchanger member;

decreasing the ambient temperature of said liquid phase in said shaded heat exchanger member;

rotating said fan so as to discharge the air within said shaded area into the atmosphere, said rotation being imported by a wind without use of electricity;

decreasing the ambient temperature of said liquid phase in said heat exchanger by discharge of the air within said shaded area;

cooling said liquid phase within said storage tank by thermal mass cooling so that the ambient temperature of said liquid phase is allowed to decrease.

4. The method of claim 3 further comprising:

venting the gas phase into the atmosphere;

pumping the liquid phase from the storage tank to a reservoir means for storing the liquid phase with a pump member.

5. The method of claim 4 wherein the step of pumping the liquid phase from the storage tank to the reservoir means includes:

measuring the liquid phase level within said storage tank;

activating said pump member once a predetermined level is reached within said storage tank;

terminating said pump member once the liquid phase level has been lowered due to said pumping.

6. The method of claim 5 wherein said recovery system further contains a temperature gauge adapted to said storage tank, and wherein the method further comprises:

monitoring the output temperature of the liquid phase being pumped from said storage tank;

adjusting the liquid level to provide for longer retention time in accordance with the temperature of the liquid phase.

7. The method of claim 6 wherein said step of venting the gas phase into the atmosphere includes:

preventing any adverse back-pressure to be delivered to the glycol dehydrator unit.

\* \* \* \* \*